United States Patent
Cliffe et al.

[11] Patent Number: 6,127,357
[45] Date of Patent: Oct. 3, 2000

[54] N-((PHENYL, BENZODIOXINYL OR N-HETEROARYLPIPERAZINYL)ALKYL)-N-(N-HETEROARYL)SUBSTITUTED CARBOXAMIDES

[75] Inventors: Ian Anthony Cliffe, Slough; Howard Langham Mansell, Burnham, both of United Kingdom

[73] Assignee: John Wyeth & Brother, Ltd., Maidenhead, United Kingdom

[21] Appl. No.: 08/438,812

[22] Filed: May 11, 1995

Related U.S. Application Data

[63] Continuation of application No. 08/172,686, Dec. 23, 1993, abandoned, which is a continuation of application No. 07/877,898, May 1, 1992, abandoned.

[30] Foreign Application Priority Data

May 2, 1991 [GB] United Kingdom .................... 9109475
Dec. 21, 1991 [GB] United Kingdom .................... 9127189

[51] Int. Cl.[7] ...................... A61K 31/496; C07D 401/12; C07D 417/04; C07D 417/12

[52] U.S. Cl. ........................ 514/210; 514/212; 514/224.2; 514/227.8; 514/230.5; 514/235.8; 514/252; 514/253; 514/254; 540/598; 544/52; 544/58.4; 544/105; 544/121; 544/295; 544/357; 544/360; 544/361; 544/363; 544/364

[58] Field of Search ..................................... 544/360, 361, 544/363, 364, 367, 368, 377, 295, 238, 121, 357, 373, 376, 52, 105, 58.4; 540/598, 595; 514/210, 212, 235.8, 252–254, 224.2, 227.8, 230.5

[56] References Cited

U.S. PATENT DOCUMENTS

| | | | |
|---|---|---|---|
| 4,684,651 | 8/1987 | Kikumoto et al. | 544/360 |
| 4,988,814 | 1/1991 | Abou-Gharbia et al. | 544/360 |
| 5,010,078 | 4/1991 | Abou-Gharbia et al. | 544/360 |
| 5,112,824 | 5/1992 | Baldwin et al. | 544/360 |
| 5,135,931 | 8/1992 | Carlier et al. | 544/360 |
| 5,723,464 | 3/1998 | Brightwell et al. | 514/254 |

FOREIGN PATENT DOCUMENTS

| | | |
|---|---|---|
| 0061149 | 9/1982 | European Pat. Off. |
| 0372657 | 6/1990 | European Pat. Off. |
| 512755 | 11/1992 | European Pat. Off. |
| 58-154573 | 9/1983 | Japan |
| 59-10517 | 1/1984 | Japan |
| 1279843 | 6/1972 | United Kingdom |

OTHER PUBLICATIONS

Cliffe et al, Chemical Abstracts, vol. 118, No. 169115 (1993) (Abstract for EP512755, Nov. 11, 1992).

Mitsubishi Derwent Abst. No. 84–052382/09 for JP 59–010517 (1984).

Mitsubishi Chem Abst. vol. 101, No. 7198 (1984)–for JP 59–010517 (1984).

Mitsubishi Derwent Abst. No. 83–797402/43 for JP 58–154573 (1983).

Mitsubishi Chem. Abst. vol. 100, No. 103390 (1984) for JP 58–154573 (1983).

*Primary Examiner*—Emily Bernhardt
*Attorney, Agent, or Firm*—Rebecca R. Barrett

[57] ABSTRACT

Piperazine derivatives of formula I

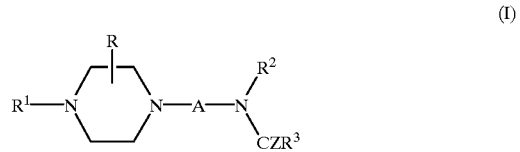

and their pharmaceutically acceptable acid addition salts are 5-$HT_{1A}$ binding agents, particularly 5-$HT_{1A}$ antagonists and may be used, for example, as anxiolytics. In the formula A is $C_{2-4}$ alkylene chain optionally substituted by lower alkyl, Z is oxygen or sulphur, R is hydrogen or lower alkyl, $R^1$ is a mono or bicyclic aryl or heteroaryl radical, $R^2$ is a mono or bicyclic heteroaryl radical and $R^3$ is hydrogen or a specified radical such as lower alkyl, cycloalkyl, aryl, heteroaryl or optionally substituted amino.

43 Claims, No Drawings

N-((PHENYL, BENZODIOXINYL OR N-HETEROARYLPIPERAZINYL)ALKYL)-N-(N-HETEROARYL)SUBSTITUTED CARBOXAMIDES

"This application is a continuation of U.S. application Ser. No. 08/172,686, filed Dec. 23, 1993, now abandoned, which, in turn, is a continuation of U.S. application Ser. No. 07/877,898, filed May 1, 1992, now abandoned."

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

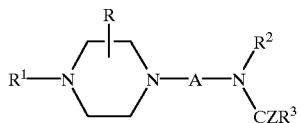

(I)

and the pharmaceutically acceptable acid addition salts thereof.

In formula (I)

A is an alkylene chain of 2 to 4 carbon atoms optionally substituted by one or more lower alkyl groups, Z is oxygen or sulphur, R is hydrogen or lower alkyl, $R^1$ is a mono or bicyclic aryl or heteroaryl radical, $R^2$ is a mono or bicyclic heteroaryl radical and $R^3$ is hydrogen, lower alkyl, cycloalkyl, cycloalkenyl, cycloalkyl(lower)alkyl, aryl, aryl(lower)alkyl, heteroaryl, heteroaryl-(lower)alkyl, a group of formula —$NR^4R^5$ [where $R^4$ is hydrogen, lower alkyl, aryl or aryl-(lower)alkyl and R is hydrogen, lower alkyl, —CO(lower)alkyl, aryl, COaryl, aryl(lower)alkyl, cycloalkyl or cycloalkyl-(lower)alkyl or $R^4$ and $R^5$ together with the nitrogen atom to which they are both attached represent a saturated heterocyclic ring which may contain a further hetero atom] or a group of formula $OR^6$ [where $R^6$ is lower alkyl, cycloalkyl, cycloalkyl(lower)alkyl, aryl, aryl(lower)alkyl, heteroaryl or heteroaryl(lower)alkyl].

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl.

Examples of cycloalkyl groups are cyclopentyl, cyclohexyl and cycloheptyl. A preferred example is cyclohexyl. Cycloalkyl groups include bicyclic, tricyclic and tetracyclic groups, eg adamantyl. Preferably the cycloalkyl group contains 3 to 12 carbon atoms.

When used herein "aryl" means an aromatic radical having 6 to 12 carbon atoms (eg phenyl or naphthyl) which optionally may be substituted by one or more substituents. Preferred substituents are lower alkyl, lower alkoxy (eg methoxy, ethoxy, propoxy, butoxy), halogen, halo(lower) alkyl (eg trifluoromethyl), nitro, nitrile, amido, (lower) alkoxycarbonyl, amino, (lower)alkylamino or di(lower) alkylamino substituents. Two substituents on the aromatic ring may be connected together to form another ring system. For example $R^1$ may be an optionally substituted tetrahydronaphthyl radical or a bicyclic oxygen-containing radical of the formula

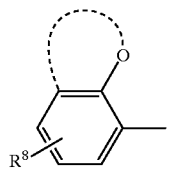

wherein the heterocyclic ring containing the oxygen atom contains a total of 5 to 7 ring members, said heterocyclic ring being saturated or unsaturated, being optionally substituted and optionally containing one or more hetero ring members (eg —O—, $NR^7$— where $R^7$ is hydrogen or lower alkyl, —S— or —$SO_2$—) in addition to the oxygen atom illustrated and wherein $R^8$ represents hydrogen or one or more same or different substituents selected from lower alkyl, halogen, oxo, hydroxy, (lower)alkoxy, hydroxy(lower)alkyl, (lower)alkoxy(lower alkyl), lower alkanoyloxy(lower alkyl), (lower)-alkylcarbonyl, (lower)alkylcarbonyl(lower) alkyl, amino, (lower)alkylamino or di(lower)alkylamino.

Preferred examples of a bicyclic oxygen-containing radical are those of the formulae (a)

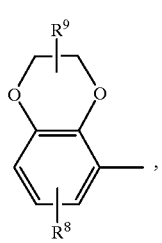

(b)

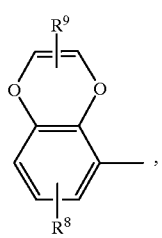

(c)

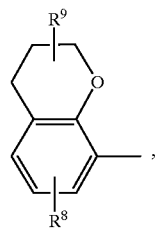

(d)

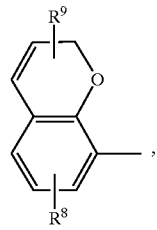

(e) 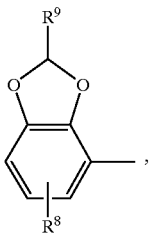

(f) 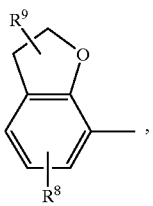

(g) 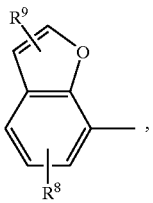

(h) 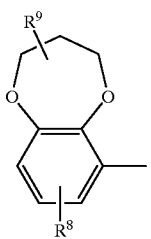

(i) 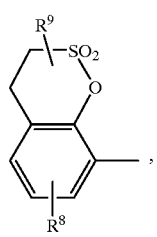

(j) 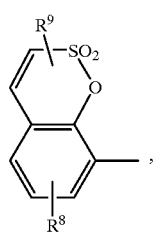

or (k) 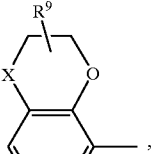

where $R^8$ is as defined above, $R^9$ has the definition of $R^8$ given above and X is —CO—, —S—, or —NR$^7$— where $R^7$ is hydrogen or lower alkyl.

When $R^1$ is an aryl radical it is preferably a phenyl radical containing a substituent in the ortho position. A preferred example of $R^1$ is o-(lower)alkoxyphenyl eg o-methoxyphenyl. $R^1$ can also be, for example a 1-naphthyl radical optionally substituted in the 2 or 7 positions by, for example, (lower)alkoxy.

Preferred examples of aryl(lower)alkyl are benzyl and phenethyl in which the phenyl rings may be substituted by substituents as given above.

The term "heteroaryl" refers to an aromatic radical containing one or more hetero atoms (eg oxygen, nitrogen, sulphur) and which may be optionally substituted by one or more substituents. Examples of suitable substituents are given above in connection with "aryl" radicals. The heteroaryl radical may, for example, contain up to 10 ring atoms. Preferably the heteroaryl radical is a monocyclic radical containing 5 to 7 ring atoms. Preferably the hetero ring contains a nitrogen hetero atom with or without one or more further hetero atoms. When $R^1$ is-a heteroaryl radical it is preferably an optionally substituted pyrimidyl (particularly 2-pyrimidyl), isoquinolinyl (particularly 1-isoquinolinyl) or 1,2-benzisothiazolyl radical. When $R^2$ is a bicyclic heteroaryl radical both rings of the radical may contain hetero ring atoms or only one ring may contain a hetero atom or atoms. In the latter instance the radical $R^2$ is connected to the rest of the molecule of formula (I) via the ring containing the hetero atom(s).

Examples of the heteroaryl radical $R^2$ include monocyclic radicals containing one hetero atom, eg optionally substituted pyridyl (particularly 2-pyridyl), monocyclic radicals containing two hetero atoms, eg thiazolyl (particularly 2-thiazolyl) and bicyclic radicals containing one or two hetero atoms eg quinolinyl or isoquinolinyl (particularly 2-quinolinyl).

When $R^4$ and $R^5$ together with the nitrogen atom to which they are both attached represent a saturated heterocyclic ring this may be, for example, azetidino, pyrrolidino, piperidino, hexahydroazepino, morpholino or piperazino which may be optionally substituted by, for example, lower alkyl, aryl or aryl(lower)alkyl.

Preferred compounds have the following substituents either independently or in combination:

(a) A is —(CH$_2$)$_2$—, —(CH$_2$)$_3$—, —(CH$_2$)$_4$— or —CH(CH$_3$).CH$_2$—

(b) R is hydrogen (c) $R^1$ is o-methoxyphenyl, o-isopropylphenyl, 4-fluoro-2-methoxyphenyl, 2,3-dihydro[1,4]benzo-dioxan-5-yl), pyrimid-2-yl, 1-naphthyl,3-(1,2-benzisothiazolyl), 1-(7-methoxynapthyl) or 1-(5,6,7,8)-tetrahydronaphthyl (d) $R^2$ is pyrid-2-yl, quinolin-2-yl or thiazol-2-yl (e) $R^3$ is lower alkyl (eg methyl or t-butyl), cycloalkyl (eg cyclohexyl), cycloalkenyl (eg cyclohexenyl), phenyl, piperidino, adamantyl, or —NHcycloalkyl (eg —NHcyclohexyl)

(f) Z is oxygen

The compounds of the invention may be prepared by methods known in the art from known starting materials or starting materials that may be prepared by conventional methods.

One method of preparing the compounds of the invention comprises acylating an amine of formula

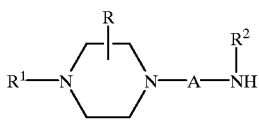

(II)

(where A, R, $R^1$ and $R^2$ have the meanings given above with an acid of formula $R^3CZOH$ (III)

(where Z and $R^3$ is as defined above) or with an acylating derivative thereof. Z is preferably oxygen. Examples of acylating derivatives include the acid halides (eg acid chlorides), azides, anhydrides, imidazolides (eg obtained from carbonyldiimidazole), activated esters or O-acyl ureas obtained from a carbodiimide such as a dialkylcarbodiimide particularly cyclohexylcarbodiimide.

Compounds in which $R^3$ is —$NR^4R^5$ are urea or thiourea derivatives and may be prepared by reacting an amine of formula (II) with the appropriate isocyanate or isothiocyanate (including an appropriate acylisocyanate or acylisothiocyanate). Ureas in which $R^4$ is —CO(lower)alkyl or —CO aryl may also be prepared by acylating the corresponding urea or thiourea in which $R^4$ is hydrogen.

The starting amine of formula (II) may be prepared by a process such as that exemplified below:

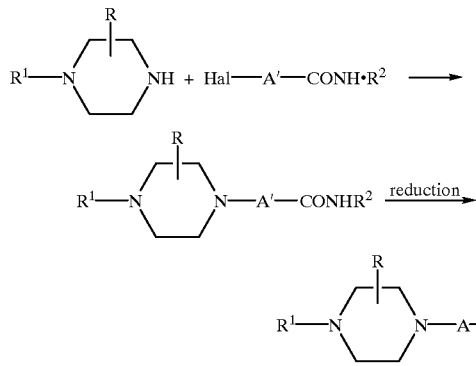

(where R, $R^1$, $R^2$ and A are as defined above, Hal is halo, particularly chloro or bromo and A is an alkylene chain of 1 to 3 carbon atoms optionally substituted by one or more lower alkyl groups). The reduction may be carried out with, for example, a boron reducing agent eg borane-dimethyl sulphide or a complex metal hydride, eg lithium aluminium hydride.

Some of the amines of formula (II) are novel. A particularly preferred novel amine, which is provided by the present invention is 1-(2-methoxyphenyl)-4-[2-(2-pyridinylamino)ethyl]-piperazine.

A further method of preparing the compounds of the invention comprises alkylating an amide of formula (IV)

(IV)

with an alkylating agent providing the group

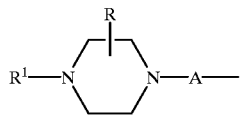

The alkylating agent may be, for example, a compound of formula

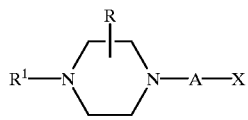

where A, R and $R^1$ are as defined above and X is a leaving group such as halogen or an alkyl — or aryl-sulphonyloxy group. Z is preferably oxygen.

A further method of preparing the compounds of the invention comprises alkylating a compound of formula

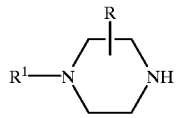

with a compound of formula $X—A NR^2.CZ.R^3$ (V)

(where A, R, $R^1$, $R^2$, $R^3$, Z and X are as defined above). Z is preferably oxygen. The starting compound of formula (V) may, for example, be prepared as exemplified below $X—A—Br+NHR^2CZR^3$ (V)

A further method of preparing the compounds of the invention comprises heteroarylating a compound of formula (VI)

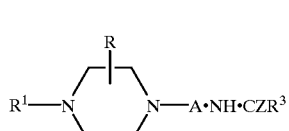

with a compound providing the heteroaryl group $R^2$. For example the compound of formula (VI) may be reacted with a fluoro compound of formula $R^2F$ eg in the presence of a strong non-nucleophilic base (eg lithium diisopropylamide).

Where $R^1$ is a group that is activated towards nucleophilic substitution the compounds of the invention may be prepared by a further method which comprises reacting the appropriate fluoro compound of formula R¹F with a piperazine compound of formula

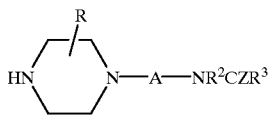

Compounds of the invention in which Z is sulphur may be prepared by sulphurisation of compounds of the invention where Z is oxygen. The compounds where Z is oxygen may, for example, be reacted with a sulphurising agent such as a mixture of phosphorus pentasulphide and potassium sulphide.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, so that some compounds can exist in different steroisomeric forms. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-HT$_{1A}$ type. In general, the compounds selectively bind to receptors of the 5-HT$_{1A}$ type to a much greater extent than they bind to other receptors such as $\alpha_1$ and $D_2$ receptors. Many exhibit activity as 5-HT$_{1A}$ antagonists in pharmacological testing. The compounds of the invention can be used for the treatment of CNS disorders, such as anxiety in mammals, particularly humans. They may also be used as antidepressants, hypotensives and as agents for regulating the sleep/wake cycle, feeding behaviour and/or sexual function.

The compounds of the invention were tested for 5-HT$_{1A}$ receptor binding activity in rat hippocampal membrane homogenate by the method of B S Alexander and M D Wood, J Pharm Pharmacol, 1988, 40, 888–891.

The compounds of Examples 3, 4, and 17, which are representative compounds of the invention, had IC$_{50}$'s of respectively 2.2, 5.8 and 3 nM in this test procedure.

The compounds are tested for 5-HT$_{1A}$ receptor antagonism activity in a test involving the antagonism of 5-carboxamidotryptamine in the guinea-pig ileum in vitro (based upon the procedure of Fozard et al, Br J Pharmac, 1985, 86, 601P). The results for representative compounds of the invention are given below. The compound of Example 3 had a pA$_2$ of 8.7 and that of Example 4 had a pA$_2$ of 7.8 and that of Example 17 had a PA$_2$ of 9.8.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "compositions" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols, eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention. Examples 1,2,7,9,10,12–16,18,19,21–29,32 and 34–45 illustrate the preparation of intermediates.

EXAMPLE 1

2-(1-(4-(2-Methoxyphenyl)piperazinyl))-N-(2-pyridinyl)acetamide

A stirred solution of 2-chloro-N-(2-pyridinyl)acetamide (9.9g, 58 mmol) in dry DMF (40 ml) at 0° C. was treated with 1-(2-methoxyphenyl)piperazine (11.1 g 58 mmol) in dry DMF (40 ml), treated with potassium carbonate (9.2g, 67 mmol), after 30 min warmed to room temperature and after 18h treated with water (400 ml). The emulsion was extracted with ether (3×200 ml) and the extracts washed with water (500 ml), dried ($Na_2So_4$) and evaporated in vacuo to give a yellow oil. Purification by chromatography (silica; ethyl acetate) gave the product (17.3g) as an oil which crystallised on standing, m.p. 86–89° C.

EXAMPLE 2

1-(2-Methoxyphenyl)-4-(2-(2-pyridinylamino)ethyl) piperazine

A solution of the product of Example 1 (13.87 g, 42.5 mmol) in THF (150 ml) was heated under reflux under Ar, treated dropwise with borane-dimethyl sulphide (8 ml, 84.3 mmol), after 2½ h treated dropwise with methanol (50 ml) and treated with ¼N—HCl (200 ml). After 1 hr the reaction mixture was cooled to room temperature, washed with ethyl acetate (2×200 ml), basified with 2N—NaOH, and extracted with ethyl acetate (2×200 ml). The extracts were dried ($Na_2SO_4$) and evaporated in vacuo to give the product as an oil (11.8 g). The product was purified by chromatography [silica, ethyl acetate-ethanol (20:1)] and converted to the salt-form with ethereal-hydrogen chloride. Crystallisation from acetonitrile gave the trihydrochloride salt of the product as white crystals, m.p. 212–214° C. (Found: C, 50.8; H, 6.7; N, 13.2 $C_{18}H_{24}N_4O.3HCl.¼H_2O$ requires C, 50.7; H, 6.5; N, 13.1%).

EXAMPLE 3

N-(2-(1-(4-(2-Methoxyphenyl)piperazinyl))ethyl)-N-(2-pyridinyl)cyclohexanecarboxamide A stirred suspension of potassium hydride, 35 wt. % suspension in mineral oil (2.99 g, ca. 26.1 mmol) in DMF (25 ml) was treated dropwise under Ar with the free base of Example 2 (2.14 g, 6.9 mmol) in DMF (15 ml). The reaction mixture was treated dropwise after 20 min with cyclohexanecarbonyl chloride (1.4 ml, 10.5 mmol), and after 1 hr treated carefully with water (200 ml), acidified with 2N—HCl (ca. 70 ml), washed with hexane (2×200 ml), basified with 2N—NaOH, and extracted with ethyl acetate (2×200 ml). The extracts were washed with brine (100 ml), dried ($Na_2SO_4$), and evaporated in vacuo to give a red oil which was purified by chromatography (silica; ethyl acetate). A solution of the oil in methanol (40 ml) was acidified with ethereal hydrogen chloride and evaporated in vacuo to give the trihydrochloride salt of the product (1.04 g), m.p. 165–172° C. (dec.)

(Found: C, 54.2; H, 7.3; N, 10.0% $C_{25}H_{34}N_4O_2.3HCl.H_2O$ requires C, 54.6; H, 7.15; N 10.2%).

EXAMPLE 4

N-Cyclohexyl-N-(2-(1-(4-(2-methoxyphenyl) piperazinyl))ethyl)-N-(2-pyridinyl)urea A stirred suspension of potassium hydride, 35 wt. % suspension in mineral oil (2.91 g, ca. 21.8 mmol) in dry DMF (20 ml) was treated dropwise with the free base of Example 2 (2.92 g, 9.4 mmol) in dry DMF (15 ml) under Ar. After 1 h the reaction mixture was treated with cyclohexyl isocyanate (1.3 ml, 10.2 mmol) and after a further 18 h treated with water (200 ml), acidified with 2N—HCl (ca. 50 ml), washed with hexane (2×200 ml), basified with 2N—NaOH, and extracted with ethyl acetate (2×200 ml). The extracts were washed with brine (200 ml), dried ($Na_2SO_4$), and evaporated in vacuo to give a brown oil which was purified by chromatography (silica; ethyl acetate, then alumina; ether). The colourless oil was dissolved in ethanol (10 ml) and the solution acidified with ethereal hydrogen chloride and evaporated in vacuo to give the trihydrochloride salt of the product as a hydrated glass containing a quarter mole of ethyl acetate (0.456 g)

(Found: C, 53.2; H, 7.5; N, 11.8. $C_{25}H_{35}N_5O_2.3HCl.H_2O.¼C_4H_8O_2$ requires C, 53.2; H, 7.2; N, 11.9%).

EXAMPLE 5

N-(2-(1-(4-(2-Methoxyphenyl)piperazinyl))ethyl)-N-(2-pyridinyl)benzamide

Benzoyl chloride (1.69 g, 12 mmol) was added cautiously to a stirred solution of Example 2 free base (1.94 g, 6 mmol) and di-isopropylethylamine (2.2 ml, 14 mmol) in dichloromethane (20 ml). The mixture was stirred under Ar for 24 h, evaporated in vacuo, and the brown oil dissolved in water (50 ml). The solution was acidified with 2N—HCl, washed with dichloromethane (3×50 ml), basified with 2N—NaOH, and extracted with dichloromethane (3×75 ml). The extracts were dried ($MgSO_4$), evaporated in vacuo, and the residue purified by chromatography [alumina; toluene-ethyl acetate (7:3)]. The oil was dissolved in ethyl acetate (10 ml) and the dihydrochloride salt of the product precipitated with ethereal hydrogen chloride as colourless crystals (1.3 g), m.p. 105–112° C.

(Found: C, 61.6; H, 6.1; N, 11.3, $C_{25}H_{28}N_4O_2$. 2HCl requires C, 61.4; H, 6.2; N, 11.5%).

EXAMPLE 6

N-(2-(1-(4-(2-Methoxyphenyl)piperazinyl))ethyl)-N-(2-pyridinyl)trimethylacetamide This compound was synthesised by an analogous method to that used for Example 5, substituting trimethylacetyl chloride (1.57 g, 13 mmol) for benzoyl chloride, to give the trihydrochloride salt of the product (1.2 g) as a white solid, m.p. 138–140° C.

(Found: C, 53.5; H, 7.3; N, 10.8. $C_{23}H_{32}N_4O_2.3HCl.½H_2O$ requires C, 53.7; H, 7.1; N, 10.9%).

EXAMPLE 7

N-(2-thiazolyl)cyclohexanecarboxamide

Cyclohexanecarbonyl chloride (4.38 g, 30 mmol) was added dropwise to a solution of 2-aminothiazole (3.00 g, 30 mmol) and di-isopropylethylamine (3.87 g, 30 mmol) in dichloromethane (50 ml) at 0° C. The mixture was warmed to room temperature, stirred for 18 h, washed with 1 N—HCl (2×50 ml) and 1 N—NaOH (2×50 ml), dried ($MgSO_4$), and evaporated in vacuo to give the product (4.59 g) as white crystals.

EXAMPLE 8

N-(2-(1-(4-(2-Methoxyphenyl)piperazinyl))ethyl)-N-(2-thiazolyl)cyclohexanecarboxamide A solution of the product of Example 7 (2.10 g, 10 mmol) in DMF was added dropwise to a stirred suspension of potassium hydride, 35 wt. % suspension in mineral oil (1.6 g, ca 14 mmol) in DMF (20 ml) under Ar. After 1 h, 1-(2-chloroethyl)-4-(2-methoxyphenyl)piperazine (2.53 g, 10 mmol) was added portionwise and the mixture stirred at 80° C. for 5 h. Saturated aq. $Na_2CO_3$ (20 ml) was added cautiously and the mixture concentrated in vacuo. The residue was taken up into ether (100 ml) and extracted with 1N—HCl (3×50 ml). The aqueous phases were basified with 1N—NaOH and extracted with ether (3×50 ml). The ethereal extracts were dried ($MgSO_4$), evaporated in vacuo, and the residue purified by chromatography (silica; ethyl acetate). The oil was dissolved in ethyl acetate (10 ml) and the dihydrochloride salt of the product precipitated with ethereal hydrogen chloride as a white solid (1.1 g), m.p. 205° C. (a phase change was observed at 80° C. and the sample decomposed at 205° C.).

(Found: C, 53.4: H, 6.8: N, 10.7. $C_{23}H_{32}N_4O_2S$ 2HCl.¾$H_2O$ requires C, 53.6; H, 7.0; N, 10.9%).

EXAMPLE 9

2-(1-(4-(4-Fluoro-2-methoxyphenyl)piperazinyl))-N-(2-pyridinyl)acetamide

A stirred solution of 2-chloro-N-(2-pyridinyl)acetamide (0.94 g, 5.5 mmol) in dry DMF (10 ml) was treated with 1-(4-fluoro-2-methoxyphenyl)piperazine (1.16 g, 5.5 mmol) and di-isopropylethylamine (1.1 ml, 6.3 mmol), and after 19h treated with water (50 ml). The emulsion was extracted with ether (2×50 ml) and the extracts washed with water (100 ml), dried ($MgSO_4$) and evaporated in vacuo to give a yellow oil. Purification by chromatography (silica; ether) gave the product (1.61 g) as colourless crystals, m.p. 110–120° C. (sample softens at 32° C.).

EXAMPLE 10

1-(4-Fluoro-2-methoxyphenyl)-4-(2-(2-pyridinylamino)ethyl)piperazine

A solution of the product of Example 9 (1.51 g, 4.4 mmol) in THF (20 ml) was heated under reflux under Ar and treated dropwise with borane-methyl sulphide complex, 2M solution in THF (4.4 ml, 8.8 mmol). After 4 h the reaction mixture was treated dropwise with methanol (10 ml) and treated with 2N—HCl (10 ml). After 1 hr the reaction mixture was cooled to room temperature, treated with water (100 ml), basified with 2N—NaOH, and extracted with ethyl acetate (2×100 ml). The extracts were washed with brine (50 ml), dried ($MgSO_4$), and evaporated in vacuo to give the product as a yellow oil (1.29 g) which was used in the next Example without further purification.

EXAMPLE 11

N-(2-(1-(4-(4-Fluoro-2-methoxyphenyl)piperazinyl))ethyl)-N-(2-pyridinyl)cyclohexanecarboxamide A stirred solution of the product of Example 10 (1.26 g, 3.8 mmol) in dichloromethane (20 ml) under Ar was treated with di-isopropylethylamine (1.4 ml, 8.4 mmol) and cyclohexanecarbonyl chloride (1 ml, 7.5 mmol), washed after 24 hr with water (20 ml), saturated aq. $NaHCO_3$, (20 ml), and water (20 ml), dried ($MgSO_4$) and evaporated in vacuo to give a yellow oil which was purified by chromatography (silica; ethyl acetate). A solution of the oil in methanol (5 ml) was acidified with ethereal hydrogen chloride and evaporated in vacuo to give the trihydrochloride salt of the product (10.5 g, 30%), m.p. 160–172° C.

(Found: C, 54.7; H, 6.4; N, 10.1% $C_{25}H_{33}FN_4O_2$.3HCl requires C, 54.6; H, 6.6; N 10.2%).

EXAMPLE 12

5-Nitro-2,3-dihydro-1,4-benzodioxin 1,2-Dibromoethane (12.0 g, 0.064 mol), potassium carbonate (17.6 g, 0.127 mol) and tetra-n-butyl ammonium bromide (1.37 g, 0.0043 mol) were added to a stirred solution of 3-nitrocatechol (6.59 g, 0.043 mol) in toluene (210 ml). The solution was heated at reflux with azeotropic removal of water for 23 h, cooled to room temperature, washed with 2N. sodium hydroxide solution (150 ml), dried ($Na_2SO_4$), and evaporated in vacuo to give an orange oil. Purification by column chromatography (silica; ether) gave the product (2.55 g), m.p. 55–59° C.

EXAMPLE 13

2,3-Dihydro-1,4-benzodioxin-5-amine

Ammonium formate (3.40 g, 0.054 mol) and 10% palladium on charcoal (1.44 g) were added to a stirred solution of the product of example 12 (2.45 g, 0.0135 mol) in methanol (15 ml). After the considerable effervescence had ceased, the mixture was filtered, evaporated in vacuo and triturated with acetonitrile. The residue was purified by chromatography (silica; ether) to give the product (1.51 g).

EXAMPLE 14

1-(2,3-Dihydro-1,4-benzodioxin-5-yl)piperazine

The solution of the product of example 13 (1.50 g, 0.010 mol) and bis(2-chloroethyl)amine hydrochloride (1.77 g 0.01 mol) in chlorobenzene (20 ml) was heated under reflux for 24 h, cooled to room temperature and evaporated in vacuo. The white solid was dissolved in aqueous sodium hydroxide (100 ml) and extracted into ethyl acetate (3×50 ml). The extracts were dried ($MgSO_4$) and evaporated in vacuo to give the product (2.00 g).

EXAMPLE 15

2-(1-(4-(2,3-Dihydro-1,4-benzodioxin-5-yl)piperazinyl))-N-(pyridin-2-yl)acetamide A stirred solution of 2-chloro-N-(2-pyridinyl)acetamide (9.9 g, 58 mmol) in dry DMF (40 ml) at 0° C. was treated with the product of example 14 (58 mmol) in dry DMF (40 ml), treated with potassium carbonate (9.2 g, 67 mmol), after 30 min warmed to room temperature and after 18 h treated with water (400 ml). The emulsion was extracted with ether (3×200 ml) and the extracts washed with water (500 ml), dried ($Na_2SO_4$) and evaporated in vacuo to give a yellow oil. Purification by chromatography (silica; ethyl acetate) gave the product as an oil.

EXAMPLE 16

1-(2,3-Dihydro-1,4-benzodioxin-5-yl)-4-(2-(2-pyridinylamino)ethyl)piperazine

A solution of the product of Example 15 (42.5 mmol) in THF (150 ml) was heated under reflux under Ar, treated dropwise with borane-dimethyl sulphide (8 ml, 84.3 mmol), after 2½ h treated dropwise with methanol (50 ml) and treated with ¼N—HCl (200 ml). After 1 h the reaction mixture was cooled to room temperature, washed with ethyl acetate (2×200 ml), basified with 2N—NaOH, and extracted with ethyl acetate (2×200 ml). The extracts were dried (Na$_2$SO$_4$) and evaporated in vacuo. Purification by chromatography, [silica; ethyl acetate —ethanol (20:1)] gave the product as an oil.

EXAMPLE 17

N-(2-(1-(4-(2,3-Dihydro-1,4-benzodioxin-5-yl)piperazinyl))ethyl)-N-(2-pyridinyl)cyclohexanecarboxamide A stirred suspension of potassium hydride, 35 wt. % suspension in mineral oil (2.99 g, ca. 26.1 mmol) in DMF (25 ml) was treated dropwise under Ar with the product of Example 16 (6.9 mmol) in DMF (15 ml). The reaction mixture was treated dropwise after 20 min with cyclohexanecarbonyl chloride (1.4 ml, 10.5 mmol), and after 1 h treated carefully with water (200 ml), acidified with 2N—HCl (ca. 70 ml), washed with hexane (2×200 ml), basified with 2N—NaOH, and extracted with ethyl acetate (2×200 ml). The extracts were washed with brine (100 ml), dried (Na$_2$SO$_4$), and evaporated in vacuo to give a red oil which was purified by chromatography (silica; ethyl acetate). A solution of the oil in methanol (40 ml) was acidified with ethereal hydrogen chloride and evaporated in vacuo to give the hydrochloride salt of the product (1.04 g), m.p. 125–131° C.

(Found: C, 62.6; H, 7.3; N, 11.0 C$_{26}$H$_{34}$N$_4$O$_2$.HCl.¾H$_2$O requires C, 62.4; H, 7.35; N 11.2%)

EXAMPLE 18

2-(1-(4-(3-(1,2-Benzisothiazolyl))piperazinyl))-N-(2-pyridinyl)acetamide

A solution of 3-piperazino-1,2-benzisothiazole (2.06 g, 6.4 mmol) in DMF (10 ml) was treated with N,N-diisopropylethylamine (2 ml, 12.3 mmol), treated with N-(2-pyridinyl)chloroacetamide (1.84 g, 9.6 mmol) in DMF (10 ml), stirred for 63 h, treated with water (150 ml), and extracted with ethyl acetate (3×50 ml). The extracts were evaporated in vacuo and the residue purified by chromatography (silica; ethyl acetate) to give the product as a foam (2.63 g).

EXAMPLE 19

2-[1-[4-[3-(1,2-Benzisothiazolyl)]]piperazinyl]-N-(2-pyridyl)ethylamine

Borane-methyl sulphide complex (10M; 4.0 ml, 40 mmol) was added dropwise to a stirred solution of the product of Example 18 (2.63 g, 7.44 mmol) in THF (26 ml) under Ar. After 18 h, the solution was cooled to 0° C., treated with methanol (10 ml), water (10 ml) and concentrated aq. HCl (10 ml), heated to reflux, cooled to room temperature and evaporated in vacuo. The yellow solid residue was treated with water (50 ml) and 12.5 N NaOH (16 ml). The mixture was extracted with CH$_2$Cl$_2$ (2×50 ml) and the extracts dried (Na$_2$SO$_4$), evaporated in vacuo and the gum chromatographed (Al$_2$O$_3$; ethyl acetate) to give the product as a clear pink oil (0.986 g).

EXAMPLE 20

N-[2-[1-[4-[3-(1,2-Benzisothiazolyl)]]piperazinyl]-ethyl]-N-(2-pyridyl)cyclohexanecarboxamide A solution of cyclohexanecarbonyl chloride (0.40 ml, 3.0 mmol) in CH$_2$Cl$_2$ (25 ml) was added dropwise to a stirred solution of the product of Example 19 (0.99 g, 2.90 mmol) and C$_5$H$_5$N (0.32 ml, 4.0 mmol) in CH$_2$Cl$_2$ (10 ml) at 0° C. under Ar. The orange solution was stirred at room temperature for 18 h, washed with water (25 ml) and saturated aq. NaHCO (10 ml), dried (Na$_2$SO$_4$) and evaporated in vacuo to give an orange oil which was chromatographed (SiO$_2$; ethyl acetate) to give the product (0.84 g). The hydrochloride salt was prepared in standard fashion and crystallised by trituration with acetonitrile to give colourless crystals (0.84 g) m.p. 174°–176° C.

Found: C, 56.92; H, 6.64; N 13.24% C$_{25}$H$_{31}$N$_5$OS. 2HCl.0.25H$_2$O requires C, 56.97; H, 6.41; N, 13.29%.

EXAMPLE 21

1-[4-Benzyl-(1-piperazinyl)]isoquinoline

A solution of 1-chloroisoquinoline (1.64 g 10 mmol) in dry DMF (5 ml) was added to a stirred solution of 1-benzylpiperazine (1.85 g, 10.5 mmol) and N,N-diisopropylethylamine (2 ml, 1.5 g, 11.5 mmol) in dry DMF (5 ml) under Ar at room temperature. The solution was stirred at room temperature for 17 h. The yellow solution was heated at 110° C. for 7 h, treated with water (100 ml) and extracted with ether (2×50 ml). The extracts were dried (Na$_2$SO$_4$) and concentrated in vacuo. The residue was chromatographed (SiO$_2$; ethyl acetate) to give the product (1.233 g).

EXAMPLE 22

1-[1-Piperazinyl]isoquinoline

Ammonium formate (1.01 g, 16.0 mmol) and 10% Pd/C 42.5 mg, 0.4 mmol, 10 mol%) were added successively to a stirred solution of the product of Example 21 (1.23 g, 4.06 mmol) in methanol (4 ml). The mixture was stirred at room temperature for 6 h and was heated at 75° C. for 16 h. Methanol (40 ml) was added and the mixture filtered through Kieselguhr, and concentrated in vacuo to give the product as a pale yellow oil.

EXAMPLE 23

1-[1-(5,6,7,8-Tetrahydro)naphthyl]piperazine

Bis(2-chloro)ethylamine hydrochloride (8.70 g, 48.7 mmol) was added to a stirred solution of 5,6,7,8-tetrahydro-1-naphthylamine (4.78 g 3.5 mmol) in chlorobenzene (90 ml). The mixture was heated at 140° C. for 38 h and cooled to room temperature. The precipitate was collected and washed with a minimum volume of chlorobenzene. Recrystallisation from ethanol gave the hydrochloride salt of the product as white crystals (2.4 g), m.p. 324° C. (decomp).

Found: C, 66.8; H, 8.5; N, 11.1. C$_{14}$H$_2$ON$_2$.HCl requires: C, 66.5; H, 8.4; N 11.1%.

EXAMPLE 24

(S)-(1-(2-(2-Pyridylamino)propyl))-4-(2-methoxyphenyl)piperazine (S)-1-(2-Aminopropyl))-4-(2-methoxyphenyl)piperazine (25 g, 100 mmol) was stirred with 2-fluoropyridine (2.6 ml, 30 mmol) in a bomb at 130° C. for 10 days. The resulting dark residue was dissolved in 150 ml water and basified with sodium hydroxide solution. The mixture was shaken with three portions of chloroform and the chloroform solution washed with water and dried over magnesium sulphate. The residual black oil (20 g) was chromatographed (silica), eluting with ethyl acetate to yield the product (1.84 g) as an oil.

EXAMPLE 25

(R)-(1-(2-(2-Pyridylamino)propyl))-4-(2-methoxyphenyl)piperazine (R)-(1-(2-(2-Pyridylamino)propyl))-4-(2-methoxyphenyl)-piperazine was prepared from (R)-(1-(2-aminopropyl))-4-(2-methoxyphenyl)piperazine (30.8 g, 123 mmol) and 2-fluoropyridine (3.0 ml, 27.4 mmol) by the method described for Example 24 as an oil (5 g).

EXAMPLE 26

3-[4-(2-Methoxyphenyl)piperazin-1-yl]propionitrile

A solution of acrylonitrile (1.06 g, 20 mmol) in ethanol (50 ml) was added to a stirred solution of 2-methoxyphenylpiperazine (3.84 g, 20 mmol) in ethanol (100 ml). After 18 h, the solvent was evaporated in vacuo to give the product (4.5 g) as a white solid.

EXAMPLE 27

4-(2-Methoxyphenyl)-1-(3-aminopropyl)piperazine

A solution of the product of Example 26 (4.4 g, 18 mmol) in concentrated ethanolic ammonia solution (150 ml) was hydrogenated over 5% rhodium on alumina powder (0.6 g) at 50 p.s.i. (about $3.4\times10^5$Pa) for 50 h to give the product (3.9 g) as a brown oil.

EXAMPLE 28

4-(2-Methoxyphenyl)-1-(3-(pyridin-2-yl)aminopropyl)piperazine

The product of Example 27 (3.9 g, 16 mmol) and 2-chloropyridine (1.82 g, 16 mmol) were heated at 160° C. in a sealed vessel for 6 h. After cooling, the residue was taken up into $CH_2Cl_2$ (50 ml) washed with aqueous NaOH (3×50 ml), dried ($MgSO_4$) and evaporated in vacuo. The residue was purified by chromatography [alumina; ethyl acetate-toluene (1:4)] to give the product (0.7 g) as a brown oil.

EXAMPLE 29

1-(2-(2-Quinolinylamino)ethyl)-4-(2-methoxyphenyl)piperazine 1-(2-aminoethyl)-4-(2-methoxyphenyl)piperazine (9.4 g, 40 mmol) and 2-chloroquinoline (6.5 g, 40 mmol) were heated at 160° C. for 3 h, then at 120° C. for 18 h in a sealed vessel. The resultant brown tar was taken up into dilute hydrochloric acid (300 ml), washed with dichloromethane (3×100 ml) basified with sodium hydroxide, extracted into dichloromethane (3×100 ml), dried ($MgSO_4$) then evaporated in vacuo to give a brown oil. The oil was purified by chromatography [alumina; ethyl acetate-toluene (1:4)] to give the product (1.8 g) as a clear oil.

EXAMPLE 30

N-(2-(1-(4-(2-Methoxyphenyl)piperazinyl))ethyl)-N-(1-piperidinylcarbonyl)-2-aminopyridine A stirred solution of the product of Example 2 (1 g, 3.2 mmol) in toluene (50 ml) was treated with diisopropylethylamine (0.84 ml, 4.8 mmol), treated dropwise with phosgene, about 12½% w/w solution in toluene (7.5 ml, about 8.6 mmol) with water-bath cooling under an atmosphere of Ar, after 1 h treated with piperidine (1.5 ml, 15 mmol), after 18 h treated with water (100 ml) and extracted with ethyl acetate (2×100 ml). The extracts were washed with water (100 ml), dried ($MgSO_4$), and evaporated in vacuo. The oil was purified by chromatography [silica, ethyl acetate-ethanol (20:1)], dissolved in ethanol (10 ml) and acidified with ethereal hydrogen chloride. Evaporation in vacuo gave the product as a pink glass (0.43 g), m.p. softens above 70° C.

Found: C, 50.2; H, 7.4; N, 10.7.$C_{24}H_{33}N_5O_2$.3HCl. 2½$H_2O$.1½ EtOH requires C, 50.1; H, 7.8; N, 10.8%

EXAMPLE 31

N-(2-(4-(2-Methoxyphenyl)piperazin-1-yl)ethyl)-N-(pyridin-2-yl)-N'-cyclohexylthiourea A suspension of the product of Example 2 (3.12 g, 10 mmol) in DMSO (50 ml) was added to KH, 35 wt. % dispersion in mineral oil (1 g, 8.7 mmol) under Ar. After 1 h, cyclohexylisothiocyanate (1.41 g, 10 mmol) was added and the mixture was stirred at 80° C. for 16 h, cooled to room temperature, and poured onto 2N—HCl (500 ml). The mixture was washed with ethyl acetate (3× 200 ml), basified with NaOH, and extracted with ethyl acetate (3×100 ml). The extracts were dried ($MgSO_4$) and evaporated in vacuo to give an oil which was purified by chromatography [alumina; ethyl acetate-hexane (1:4)]and radial chromatography [silica; chloroform-ethanol (100:1)] to give the product (0.1 g) as an oil.

(Found: C, 66.3; H, 7.8: N, 15.4. $C_{25}H_{35}N_5OS$ requires C, 66.2; H, 7.8; N, 15.4%).

EXAMPLE 32

2-(1-(4-(2-Hydroxyphenyl)piperazinyl))-N-(2-pyridinyl)ethylamine

The product of Example 2 (5.25 g, 16.8 mmol) in DMF (40 ml) was treated with potassium tert-butoxide (4.53 g, 40 mmol) under Ar, treated with propanethiol (3.14 g, 41.3 mmol), stirred at 100° C. for 18 h, cooled to room temperature, and poured onto water (200 ml). The mixture was extracted with ethyl acetate (3×80 ml) and the organic phases combined, washed with water (40 ml), dried ($MgSO_4$) and evaporated in vacuo. Purification by chromatography [alumina; hexane-ethyl acetate (1:1)] gave the product as an oil (2.79 g). The trihydrochloride salt was a colourless solid, m.p. 260–265° C.

EXAMPLE 33

N-(2-(4-(2-Hydroxyphenyl)-1-piperazinyl)ethyl)-N-(2-pyridinyl)cyclohexanecarboxamide A solution of the product of Example 32 (0.87 g, 2.9 mmol) in dichloromethane (10 ml) was treated with pyridine (0.46 g, 5.8 mmol) and cyclohexanecarbonyl chloride (0.85 g, 5.8 mmol). The mixture was stirred for 18 h, evaporated in vacuo, treated with 10% NaOH (10 ml) and ethanol (10 ml), stirred for 2 h, acidified with dil. HCl (which cleaved the phenol ester), basified with saturated aq. $NaHCO_3$, and extracted with dichloromethane (3×30 ml). The extracts were washed with water (30 ml), dried ($MgSO_4$), and evaporated in vacuo. The oil was purified by chromatography (silica; ethyl acetate) to give the product (1.09 g) as an oil. The hydrochloride salt was formed in the usual manner as a colourless powder, m.p. 220–223° C.

(Found: C, 61.5; H, 7.6; N, 11.4. $C_{24}H_{32}N_4O_2.1\frac{1}{2}HCl$ $\frac{1}{4}H_2O$ requires C, 61.6; H, 7.3: N, 12.0%

EXAMPLES 34–39

The following compounds were prepared by a procedure which was analogous to that described in Example 18.

(a) EXAMPLE 34

N-(2-Pyridinyl)-2-(1-(4-(1-naphthyl)piperazinyl))-acetamide was prepared from 1-(1-naphthyl)piperazine hydrochloride (2.49 g, 10 mmol) and N-(2-pyridinyl) chloroacetamide (1.69 g, 9.9 mmol) as colourless crystals (3.01 g), m.p. 171–173° C.

(Found: C, 72.5; H, 6.35; N, 16–1. $C_{21}H_{22}N_4O$ requires C, 72.8; H, 6.4; N, 16.2%)

(b) EXAMPLE 35

2-(1-(4-(2-Methylphenyl)piperazinyl))-N-(2-pyridinyl)-acetamide was prepared from ortho-tolylpiperazine hydrochloride (3.19 g, 15 mmol) and N-(2-pyridinyl)-2-chloroacetamide (2.56 g, 15.0 mmol) as a yellow gum (4.63 g).

(c) EXAMPLE 36

2-(1-(4-(1-Isoquinolinyl)piperazinyl))-N-(2-pyridyl)-acetamide was prepared from the product of Example 22 (707 mg, 3.3 mmol) and N-(2-pyridyl)chloroacetamide (568 mg, 3.33 mmol) as a yellow oil (1.16 g)

(d) EXAMPLE 37

2-(1-(4-(1-(7-Methoxy)naphthyl)piperazinyl))-N-(2-pyridyl)acetamide was prepared from 1-[1-(7-methoxy)] naphthyl piperazine (3.33 g, 13.8 mmol) and N-(2-pyridyl) chloroacetamide (1.88 g, 11.0 mmol), as a solid (3.125 g) m.p. 142°–144° C.

(Found: C, 68.6; H, 6.6; N 14.3 $C_{22}H_{24}N_4O_2O.5H_2O$ requires: C, 68.55; H, 6.5; N, 14.5%)

(e) EXAMPLE 38

2-(1-(4-(1-(2-Methoxy)naphthyl)piperazinyl))-N-(2-pyridyl)acetamide was prepared from 1-[1-(2-methoxy) naphthyl]piperazine hydrochloride three quarters hydrate (1.75 g, 5.99 mmol) and N-(2-pyridyl)chloroacetamide (1.08 g, 6.33 mmol) as a solid (1.71 g), m.p. 184–185° C. (from ether)

(Found: C, 69.9; H, 6.5; N, 14.8 $C_{22}H_{24}N_4O_2$ requires C, 70.2; H, 6.4; N, 14.9%)

(f) EXAMPLE 39

2-(1-(4-(1-(5,6,7,8-Tetrahydro)naphthyl)piperazinyl))-N-(2-pyridyl)acetamide was prepared from the product of Example 23 (2.88 g, 9.96 mmol) and N-(2-pyridyl) chloroacetamide as a colourless gum (2.50 g)

EXAMPLES 40–45

The following compounds were prepared by a procedure which was analogous to that described for Example 19.

(a) EXAMPLE 40

2-(1-(4-(1-Napthyl))piperazinyl)-N-(2-pyridinyl)-ethylamine was prepared from the product of Example 34 (2.965 g, 8.6 mmol) and borane-methyl sulphide complex (10 M; 4.0 ml, 40 mmol) as an oil (2.33 g)

(b) EXAMPLE 41

2-(1-(4-(2-Methylphenyl))piperazinyl)-N-(2-pyridinyl)-ethylamine was prepared from the product of Example 35 (4.63 g, 14.9 mmol) as a colourless oil (3.235 g).

(c) EXAMPLE 42

2-[1-[4-(1-Isoquinolinyl)piperazinyl]]-N-(2-pyridyl)-ethylamine was prepared from the product of Example 36 (975 mg, 2.8 mmol) and borane-methyl sulphide complex (10 M; 1.4 ml, 14 mmol) as an oil (0.695 g)

(d) EXAMPLE 43

2-[1-[4-[1-(7-Methoxy)naphthyl]]piperazinyl]-N-(2-pyridyl)ethylamine was prepared from the product of Example 37 (3.0 g, 8.0 mmol) and borane-methyl sulphide complex (10 M; 4.0 ml, 40 mmol) as an oil (2.57 g).

(e) EXAMPLE 44

2-[1-[4-[1-(2-Methoxy)naphthyl]]piperazinyl]-N-(2-pyridyl)ethylamine was prepared from the product of Example 38 (1.665 g, 4.4 mmol) and borane-methyl sulphide complex (2.4 ml, 24 mmol) as a yellow oil (1.229 g).

(f) EXAMPLE 45

2-[1-[4-[1-(5,6,7,8-Tetrahydro)naphthyl]]piperazinyl]-N-(2-pyridyl)ethylamine was prepared from the product of Example 39 (2.50 g, 7.1 mmol) and borane-methyl sulphide complex (10 M; 3.8 ml, 38 mmol) as a colourless gum (1.96 g).

EXAMPLES 46–65

The following compounds were prepared by a procedure analogous to that described for Example 20

(a) EXAMPLE 46

N-(2-(1-(4-(1-Naphthyl))piperazinyl)ethyl)-N-($^2$-pyridyl) cyclohexanecarboxamide was prepared from the product of Example 40 (2.33 g, 7.0 mmol) and cyclohexanecarbonyl chloride (0.94 ml, 7.0 mmol). The dihydrochloride salt was produced as a colourless solid (2.56 g), m.p. 188–190° C.

(Found: C, 65.3; H, 7.1; N, 10.8. $C_{28}H_{34}N_4O.2HCl$ requires C, 65.2; H, 7.0; N, 10.9%).

(b) EXAMPLE 47

N-(2-(1-(4-(2-Methylphenyl))piperazinyl)ethyl)-N-(2-pyridinyl)cyclohexanecarboxamide was prepared from the product of Example 41 (3.235 g, 10.9 mmol) as a dihydrochloride salt (3.66 g), m.p. 191–199° C.

(Found: C, 60.3; H, 7;65; N, 11.3 $C_{25}H_{34}N_4O$ 2HCl. $H_2O$ requires C, 60.4; H, 7.7; N, 11.3%).

(c) EXAMPLE 48

N-(2-(1-(4-(2-Fluorophenyl))piperazinyl)ethyl)-N-(2-pyridinyl)cyclohexanecarboxamide maleate hydrate was prepared as a white solid, m.p. 121–127° C.

(Found: C, 61.75; H, 6.7; N, 10.2 $C_{24}H_{31}FN_4O$ requires C, 61.75; H, 6.85; N, 10.3%)

(d) EXAMPLE 49

N-[2-[1-[4-(1-Isoquinolinyl)]piperazinyl]ethyl]-N-(2-pyridinyl)cyclohexanecarboxamide was prepared from the product of Example 42 (695 mg, 2.1 mmol) and cyclohexanecarbonyl chloride (0.3 ml, 2.2 mmol). The trihydrochloride salt was a colourless solid (0.392 g) m.p. 145° C.

(Found: C, 55.35; H, 7.01; N, 11.99 $C_{27}H_{33}N_5O$. 3HCl.2H$_2$O requires C, 55.06; H, 6.85; N, 11.89%)

(e) EXAMPLE 50

N-[2-[1-[4-[1-(7-Methoxy)naphthyl]]piperazinyl]ethyl]-N-(2-pyridyl)cyclohexanecarboxamide was prepared from the product of Example 43 (2.57 g, 7.1 mmol) and cyclohexane carbonyl chloride (1.75 g, 12 mmol). The hydrochloride salt was a low melting solid (2.36 g) m.p. 90° C. (slowly decomposes above this temperature).

(Found: C, 66.17; H, 7.35; N, 10.38; $C_{29}H_{36}N_4O_2$ HCl. H$_2$O requires C, 66.08; H, 7.46; N, 10.63%).

(f) EXAMPLE 51

N-(2-(1-(4-(2-Methoxyphenyl)piperazinyl))ethyl)-N-(2-pyridyl)adamantane-1-carboxamide was prepared from the product of Example 2 and adamantane-1-carbonyl chloride. The dihydrochloride salt was a white solid, m.p. 132–136° C.

(Found: C, 58.6; H, 7.5; N, 9.2. $C_{29}H_{38}N_4O_2$. 2HCl. 2½H$_2$O requires C, 58.8; H, 7.65; N, 9.45%).

(g) EXAMPLE 52

N-[2-[1-[4-[1-(2-Methoxy)naphthyl]]piperazinyl]ethyl]-N-[2-pyridyl)cyclohexanecarboxamide was prepared from the product of Example 44 (1.23 g, 3.4 mmol) and cyclohexanecarbonyl chloride (0.7 ml, 0.8 g, 5.2 mmol). The dihydrochloride salt was obtained as colourless crystals (0.83 g), m.p. 151–156° C.

(Found: C, 63.6; H, 7.1; N, 10.6. $C_{29}H_{36}N_4O_2$.2HCl requires C, 63.85; H, 7.0; N, 10.3%).

(h) EXAMPLE 53

N-[2-[1-[4-[1-(5,6,7,8-Tetrahydro)naphthyl]]-piperazinyl]ethyl]-N-(2-pyridyl)cyclohexanecarboxamide was prepared from the product of Example 45 (1.96 g, 5.8 mmol) and cyclohexanecarbonyl chloride (1 ml, 1.1 g, 7.5 mmol). The dihydrochloride salt was obtained (2.21 g), m.p. 178–180° C.

(Found: C, 64.6; H, 7.8; N, 10.9 $C_{28}H_{38}N_4O$.2HCl requires C, 64.7; H, 7.8; N, 10.8%)

(i) EXAMPLE 54

(S)-N-(1-Methyl-2-(4-(2-methoxyphenyl)-1-piperazinyl) ethyl)-N-(2-pyridinyl)cyclohexane carboxamide was prepared from the product of Example 24 (1.84 g, 5.6 mmol) and cyclohexanecarbonyl chloride (0.8 ml, 5.6 mmol). The trihydrochloride salt was prepared as crystals (1.29 g) m.p. 178–180° C., $[\alpha]_D^{26}$=+61° (methanol)

(Found: C, 57.7; H, 7.5; N , 10.32 $C_{26}H_{36}N_4O_2$. 3HCl requires C, 57.2; H, 7.2; N, 10.26%)

(j) EXAMPLE 55

(R)-N-(1-Methyl-2-(4-(2-methoxyphenyl)-1-piperazinyl) ethyl)-N-(2-pyridinyl)cyclohexane carboxamide was prepared from the product of Example 25 (1.87 g, 5.7 mmol) and cyclohexanecarbonyl chloride (0.8 ml, 5.6 mmol). The dihydrochloride salt was prepared as crystals (2.1 g), m.p. 175–180° C., $[\alpha]_D^{26}$=–60° (methanol)

(Found: C, 59.8; H, 7.8; N, 10.45 $C_{26}H_{36}N_4O_2$. 2HCl.¾H$_2$O requires C, 59.7; H, 7.6; N, 10.7%).

(k) EXAMPLE 56

N-[3-[4-(2-Methoxyphenyl)-1-piperazinyl]propyl]-N-(2-pyridinyl)cyclohexanecarboxamide was prepared from the product of Example 28 (0.7 g, 2.1 mmol) and cyclohexanecarbonyl chloride (0.63 g, 4.3 mmol). The trihydrochloride salt was a white solid (0.9 g), m.p. 137–141° C.

(Found: C, 55.6; H, 7.3; N, 9.8 $C_{26}H_{36}N_4O_2$. 3HCl.H$_2$O requires C, 55.4; H, 7.3; N, 9.9%).

(l) EXAMPLE 57

N-(2-(4-(2-Methoxyphenyl)-1-piperazinyl)ethyl)-N-(2-quinolinyl)cyclohexane carboxamide was prepared from the product of Example 29 (1.8 g, 5 mmol) and cyclohexanecarbonyl chloride (1.42 ml, 10 mmol). The monohydrochloride salt was a white solid (2.31 g), m.p. 189–192° C.

(Found: C, 66.7; H, 7.3; N, 10.5; $C_{29}H_{36}N_4O_2$. HCl. ¾H$_2$O requires C, 66.6; H, 7.4; N, 10.7%).

(m) EXAMPLE 58

(Rac)-N-(2-(4-(2-Methoxyphenyl)-1-piperazinyl) propyl)-N-(2-pyridyl)cyclohexanecarboxamide was prepared from (rac)-4-(2-methoxyphenyl)-1-(2-(1-(2-pyridylamino)-propyl))piperazine (2.28 g, 7 mmol) and cyclohexanecarbonyl chloride (1.03 ml, 7.7 mmol). The dihydrochloride salt (0.68 g) was obtained, m.p. 195–196° C. (from ethanol-ether)

(Found: C, 60.7; H, 7.2; N, 10.9 $C_{26}H_{36}N_4O_2$.2HCl. ¼H$_2$O requires C, 60.75; H, 7.55; N, 10.9%).

(n) EXAMPLE 59

(S)-N-(2-(4-(2-Methoxyphenyl)-1-piperazinyl)propyl)-N-(2-pyridyl)cyclohexanecarboxamide was prepared from (S)-4-(2-methoxyphenyl)-1-(2-(1-(2-pyridylamino)-propyl))piperazine [itself prepared from (R)-2-chloropropionyl chloride] by a method analogous to that used for Example 58. The trihydrochloride salt was a white solid, m.p. 129–130° C., $[\alpha]_D^{25}$=–25° (c=1, methanol)

(Found: C, 54.7; H, 7.2; N, 9.5 $C_{26}H_{36}N_4O_2$. 3HCl. 1½H$_2$O requires C, 54.5; H, 7.4; N, 9.8%).

(o) EXAMPLE 60

(R)-N-(2-(4-(2-Methoxyphenyl)-1-piperazinyl)propyl-N-(2-pyridyl)cyclohexanecarboxamide was prepared in a fashion similar to that used for Example 59.

(p) EXAMPLE 61

N-(2-(4-Phenyl-1-piperazinyl)ethyl)-N-(2-pyridinyl)-cyclohexanecarboxamide was prepared from 2-(4-phenyl-1-piperazinyl)-N-(2-pyridyl)ethylamine and cyclohexanecarbonyl chloride. The trihydrochloride salt was a white solid,, m.p. 198–200° C.

(Found: C, 57.2; H, 7.1; N, 11.1 $C_{24}H_{32}N_4O$. 3HCl requires C, 57.4; H, 7.0; N, 11.2%).

(q) EXAMPLE 62

N-(2-(4-(2-Isopropylphenyl)-1-piperazinyl)ethyl)-N-(2-pyridyl)cyclohexanecarboxamide was prepared from 2-(4-(2-isopropylphenyl)-1-piperazinyl)-N-(2-pyridyl)-ethylamine and cyclohexanecarbonyl chloride. The hydrochloride salt was a colourless powder, m.p. 168–170 ° C.

(Found: C, 67.15; H, 8.2; N, 11.5 $C_{27}H_{38}N_4O$.HCl.¾H$_2$O requires C, 66.9; H, 8.4; N, 11.6%).

(r) EXAMPLE 63

N-(2-(4-(2-Methoxyphenyl)-1-piperazinyl)ethyl)-N-(4-pyridinyl)cyclohexane carboxamide was prepared from 2-(4-(2-methoxyphenyl-1-piperazinyl))-N-(4-pyridyl)-ethylamine (0.39 g, 1.2 mmol) and cyclohexanecarbonyl chloride (0.37 ml, 2.5 mmol). The trihydrochloride salt (0.15 g) was a colourless solid, m.p. 151–1530° C.

(Found: C, 55.7; H. 7.3; N, 10.2 $C_{25}H_{34}N_4O_2$. 3HCl. ½$H_2O$ requires C, 55.5; H, 7.1; N, 10.4).

(s) EXAMPLE 64

N-(2-(4-(2-Methoxyphenyl)-1-piperazinyl)ethyl)-N-(3-pyridyl)cyclohexanecarboxamide was prepared from 2-(4-(2-methoxyphenyl)-1-piperazinyl)-N-(3-pyridyl)-ethylamine and cyclohexanecarbonyl chloride. The dihydrochloride salt was a hygroscopic white solid, m.p. 138–140° C.

(Found: C, 56.8; H, 7.8; N, 10.5 $C_{25}H_{34}N_4O_2$.2HCl. 2$H_2O$ requires C, 56.7; H, 7.2; N, 10.6%).

(t) EXAMPLE 65

N-(2-(4-(2-Methoxyphenyl)piperazin-1-yl)ethyl)-N-(2-pyridinyl)cyclohex-1-enecarboxamide was prepared from the product of Example 2, (1.49 g, 5 mmol) and cyclohex-1-enecarbonyl chloride (1.08 g, 7.5 mmol) as a clear oil (Found: C, 71.3: H, 7.9; N, 13.0 $C_{25}H_{32}N_4O_2$ requires C, 71.4; H, 7.7; N, 13.3%)

EXAMPLE 66

N-(2-(4-(2-Methoxyphenyl)-1-piperazinyl)ethyl)-N-(2-pyridinyl)cyclohexane thiocarboxamide Phosphorous pentasulphide (2.0 g, 4.5 mmol) and sodium carbonate (0.47 g, 4.5 mmol) were added to THF (30 ml) and the resultant mixture was stirred vigorously with gentle warming until complete dissolution (30 min). The product of Example 3 (1.5 g, 3.55 mmol) in THF (10 ml) was added and the resultant mixture was stirred at room temperature for 16 h, boiled at reflux for 3 h and cooled to room temperature. Lawesson's reagent (1.5 g, 3.71 mmol) and dioxane (30 ml) were added and the mixture was boiled at reflux for 4 h. The cooled reaction mixture was washed into a solution of sodium hydroxide (10%, 100 ml) and dichloromethane (200 ml). The organic layer was separated and the aqueous layer extracted with dichloromethane (3×100 ml). The combined extracts were washed with brine (1×200 ml), dried (MgSO$_4$), filtered and concentrated in vacuo. The resultant oil (1.0 g) was chromatographed on silica gel using dichloromethane and then 2% methanol in dichloromethane as eluents to afford an oil (280 mg). This oil was rechromatographed on alumina twice using dichloromethane as eluent to give an oil (50 mg). This was dissolved in ethanol and the dihydrochloride salt of the product was crystallised by the addition of ethereal HCl (50 mg), m.p. 108–110° C.

(Found: C, 58.5; H, 7.4; N, 10.85 $C_{25}H_{34}N_4OS$ 2HCl requires C, 58.7; H, 7.1; N, 10.95%).

What is claimed is:

1. A compound of the formula

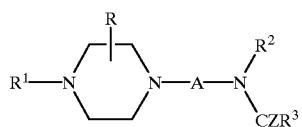

I or a pharmaceutically acceptable acid addition salt thereof, wherein

A is an alkylene chain of 2 to 4 carbon atoms optionally substituted by one or more lower alkyl groups;

Z is oxygen or sulphur;

R is hydrogen or lower alkyl;

$R^1$ is aryl, tetrahydronaphthyl, heteroaryl, wherein aryl is phenyl or naphthyl each of which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, and heteroaryl is a monocyclic aromatic heterocyclic ring having 5 ring members and having as heteroatoms one or two N atoms or one N atom and one O or S atom, or a monocyclic aromatic heterocyclic ring having 6 ring members and having as heteroatoms one or two N atoms, or a bicyclic aromatic heterocyclic ring system having one such 5 or 6 membered monocyclic aromatic heterocyclic ring fused to a benzene ring, wherein such heteroaryl or tetrahydronaphthyl ring may be optionally substituted as for aryl, or $R^1$ is a bicyclic oxygen-containing aryl radical of the formula

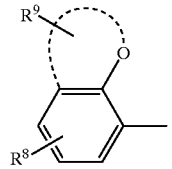

wherein the heterocyclic oxygen-containing ring has 5 to 7 ring members, said heterocyclic ring being non-aromatic and optionally having one further hetero ring member selected from —O—, —S—, —SO$_2$ or NR$^7$, wherein $R^7$ is hydrogen or lower alkyl and wherein $R^8$ and $R^9$ represent hydrogen or one or more substituents independently selected from lower alkyl, halogen, hydroxy, loweralkoxy, hydroxyloweralkyl, loweralkoxyloweralkyl, loweralkanoyloxy (loweralkyl), loweralkylcarbonyl, loweralkylcarbonyl (loweralkyl), amino, loweralkylamino or di-loweralkylamino, or $R^1$ is an bicyclic oxygen-containing aryl radical of the formula

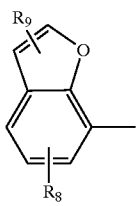

wherein $R^8$ and $R^9$ are as defined above; $R^2$ is a monocyclic aromatic heterocyclic ring having 6 members and having as heteroatoms one or two N atoms or a bicyclic aromatic heterocyclic ring system having one such 6 membered monocyclic aromatic heterocyclic ring fused to a benzene ring, which may be optionally substituted as for aryl, provided that, said bicyclic heterocyclic radical is connected to the amino nitrogen of formula I via such heterocyclic ring; and $R^3$ is hydrogen, lower alkyl, cycloalkyl, cycloalkenyl, cycloalkyl(loweralkyl), aryl, aryl(loweralkyl), a group of formula —$NR^4R^5$, or a group of formula $OR^6$, in which $R^4$ is hydrogen, lower alkyl, aryl or aryl (loweralkyl) and $R^5$ is hydrogen, lower alkyl, —CO (loweralkyl), aryl, —COaryl, aryl(loweralkyl), cycloalkyl or cycloalkyl(loweralkyl), or $R^4$ and $R^5$ together with the nitrogen atom to which they are both attached represent azetidino, pyrrolidino, piperidino, hexahydroazepino, morpholino or piperazino which may be optionally substituted by lower alkyl, aryl or aryl(loweralkyl), and $R^6$ is lower alkyl, cycloalkyl, cycloalkyl(loweralkyl), aryl, or aryl(loweralkyl), wherein aryl is as defined for $R^1$ and cycloalkyl or cycloalkenyl is a mono-, bi-, tri-, or tetracyclic hydrocarbon group of 3 to 12 carbon atoms.

2. A compound as claimed in claim 1 in which A is —$(CH_2)_2$—, —$(CH_2)_3$—, —$(CH_2)_4$— or —$CH(CH_3)$ $.CH_2$—.

3. A compound as claimed in claim 1 in which R is hydrogen.

4. A compound as claimed in claim 1 in which $R^1$ is o-methoxyphenyl, o-isopropylphenyl, 4-fluoro-2-methoxyphenyl, 2,3-dihydro[1,4]-benzodioxan-5-yl, pyrimid-2-yl, 1-naphthyl, 3-(1,2-benzisothiazolyl), 1-(7-methoxynaphthyl) or 1-(5,6,7,8-tetrahydro)naphthyl.

5. A compound as claimed in claim 1 in which $R^2$ is pyridyl-2-yl, quinolin-2-yl or thiazol-2-yl.

6. A compound as claimed in claim 1 in which $R^3$ is lower alkyl, cycloalkyl, cycloalkenyl, phenyl, piperidino or -NHcycloalkyl.

7. A compound as claimed in claim 1 which is N-(2-(1-(4-(2-methoxyphenyl)piperazinyl))ethyl)-N-(2-pyridinyl)cyclohexanecarboxamide or a pharmaceutically acceptable salt thereof.

8. A compound as claimed in claim 1 which is N-cyclohexyl-N-(2-(1-(4-(2-methoxyphenyl)-piperazinyl))ethyl)-N-(2-pyridinyl)urea or a pharmaceutically acceptable salt thereof.

9. A compound as claimed in claim 1 which is N-(2-(1-(4-(2-methoxyphenyl)piperazinyl))ethyl)-N-(2-pyridinyl)benzamide or a pharmaceutically acceptable salt thereof.

10. A compound as claimed in claim 1 which is N-(2-(1-(4-(2-methoxyphenyl)piperazinyl))ethyl)-N-(2-pyridinyl)trimethylacetamide or a pharmaceutically acceptable salt thereof.

11. A compound as claimed in claim 1 which is N-(2-(1-(4-(2-methoxyphenyl)piperazinyl))ethyl)-N-(2-thiazolyl)cyclohexanecarboxamide or a pharmaceutically acceptable salt thereof.

12. A compound as claimed in claim 1 which is N-(2-(1-(4-(4-fluoro-2-methoxyphenyl)piperazinyl))-ethyl)-N-(2-pyridinyl)cyclohexanecarboxamide or a pharmaceutically acceptable salt thereof.

13. A compound as claimed in claim 1 which is N-(2-(1-(4-(2,3-dihydro-1,4-benzodioxin-5-yl)-piperazinyl))ethyl)-N-(2-pyridinyl)cyclohexanecarboxamide or a pharmaceutically acceptable salt thereof.

14. A compound as claimed in claim 1 which is N-[2-[1-[4-[3-(1,2-benzisothiazolyl)]]piperazinyl]-ethyl]-N-(2-pyridyl)cyclohexanecarboxamide or a pharmaceutically acceptable salt thereof.

15. A compound as claimed in claim 1 which is N-(2-(1-(4-(2-methoxyphenyl)piperazinyl))ethyl)-N-(1-piperidinylcarbonyl)-2-aminopyridine or a pharmaceutically acceptable salt thereof.

16. A compound as claimed in claim 1 which is N-(2-(4-(2-methoxyphenyl)piperazin-1-yl)ethyl)-N-(pyridin-2-yl)-N'-cyclohexylthiourea or a pharmaceutically acceptable salt thereof.

17. A compound as claimed in claim 1 which is N-(2-(4-(2-hydroxyphenyl)-1-piperazinyl)ethyl)-N-(2-pyridinyl) cyclohexanecarboxamide or a pharmaceutically acceptable salt thereof.

18. A compound as claimed in claim 1 which is N-(2-(1-(4-(1-naphthyl))piperazinyl)ethyl)-N-(2-pyridyl) cyclohexanecarboxamide or a pharmaceutically acceptable salt thereof.

19. A compound as claimed in claim 1 which is N-(2-(1-(4-(2-methylphenyl))piperazinyl)ethyl)-N-(2-pyridinyl) cyclohexanecarboxamide or a pharmaceutically acceptable salt thereof.

20. A compound as claimed in claim 1 which is N-(2-(1-(4-(2-fluorophenyl))piperazinyl)ethyl)-N-(2-pyridinyl) cyclohexanecarboxamide or a pharmaceutically acceptable salt thereof.

21. A compound as claimed in claim 1 which is N-[2-[1-[4-(1-isoquinolinyl)]piperazinyl]ethyl]-N-(2-pyridinyl) cyclohexanecarboxamide or a pharmaceutically acceptable salt thereof.

22. A compound as claimed in claim 1 which is N-[2-[1-[4-[1-(7-methoxy)naphthyl]]piperazinyl]ethyl]-N-(2-pyridyl)cyclohexanecarboxamide or a pharmaceutically acceptable salt thereof.

23. A compound as claimed in claim 1 which is N-(2-(1-(4-(2-methoxyphenyl)piperazinyl))ethyl)-N-(2 -pyridyl) adamantane-1-carboxamide or a pharmaceutically acceptable salt thereof.

24. A compound as claimed in claim 1 which is N-[2-[1-[4-[1-(2-methoxy)naphthyl]]piperazinyl]ethyl]-N-[2-pyridyl)cyclohexanecarboxamide or a pharmaceutically acceptable salt thereof.

25. A compound as claimed in claim 1 which is N-[2-[1-[4-[1-(5,6,7,8-tetrahydro)naphthyl]]-piperazinyl]ethyl]-N-(2-pyridyl)cyclohexanecarboxamide or a pharmaceutically acceptable salt thereof.

26. A compound as claimed in claim 1 which is (S)-N-(1-methyl-2-(4-(2-methoxyphenyl)-1-piperazinyl)ethyl)-N-(2-pyridinyl)cyclohexane carboxamide or a pharmaceutically acceptable salt thereof.

27. A compound as claimed in claim 1 which is (R)-N-(1-methyl-2-(4-(2-methoxyphenyl)-1-piperazinyl)ethyl)-N-(2-pyridinyl)cyclohexane carboxamide or a pharmaceutically acceptable salt thereof.

28. A compound as claimed in claim 1 which is N-[3-[4-(2-methoxyphenyl)-1-piperazinyl]propyl]-N-(2-pyridinyl)cyclohexanecarboxamide or a pharmaceutically acceptable salt thereof.

29. A compound as claimed in claim 1 which is N-(2-(4-(2-methoxyphenyl)-1-piperazinyl)ethyl)-N-(2-quinolinyl)cyclohexane carboxamide or a pharmaceutically acceptable salt thereof.

30. A compound as claimed in claim 1 which is (Rac)-N-(2-(4-(2-methoxyphenyl)-1-piperazinyl)propyl)-N-(2-pyridyl)cyclohexanecarboxamide or a pharmaceutically acceptable salt thereof.

31. A compound as claimed in claim 1 which is (S)-N-(2-(4-(2-methoxyphenyl)-1-piperazinyl)propyl)-N-(2-pyridyl)cyclohexanecarboxamide or a pharmaceutically acceptable salt thereof.

32. A compound as claimed in claim 1 which is (R)-N-(2-(4-(2-methoxyphenyl)-1-piperazinyl)propyl-N-(2-pyridyl)cyclohexanecarboxamide or a pharmaceutically acceptable salt thereof.

33. A compound as claimed in claim 1 which is N-(2-(4-phenyl-1-piperazinyl)ethyl)-N-(2-pyridinyl)-cyclohexanecarboxamide or a pharmaceutically acceptable salt thereof.

34. A compound as claimed in claim 1 which is N-(2-(4-(2-isopropylphenyl)-1-piperazinyl)ethyl)-N-(2-pyridyl)cyclohexanecarboxamide or a pharmaceutically acceptable salt thereof.

35. A compound as claimed in claim 1 which is N-(2-(4-(2-methoxyphenyl)-1-piperazinyl)ethyl)-N-(4-pyridinyl)cyclohexane carboxamide or a pharmaceutically acceptable salt thereof.

36. A compound as claimed in claim 1 which is N-(2-(4-(2-methoxyphenyl)-1-piperazinyl)ethyl)-N-(3-pyridyl)cyclohexanecarboxamide or a pharmaceutically acceptable salt thereof.

37. A compound as claimed in claim 1 which is N-(2-(4-(2-methoxyphenyl)piperazin-1-yl)ethyl)-N-(2-pyridinyl)cyclohex-1-enecarboxamide or a pharmaceutically acceptable salt thereof.

38. A compound as claimed in claim 1 which is N-(2-(4-(2-methoxyphenyl)-1-piperazinyl)ethyl)-N-(2-pyridinyl)cyclohexane thiocarboxamide or a pharmaceutically acceptable salt thereof.

39. A compound of the formula

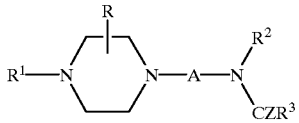

I or a pharmaceutically acceptable acid addition salt thereof, wherein

A is an alkylene chain of 2 to 4 carbon atoms optionally substituted by one or more lower alkyl groups;

Z is oxygen or sulphur,

R is hydrogen or lower alkyl;

$R^1$ is aryl, tetrahydronaphthyl, heteroaxyl, wherein aryl, is phenyl or naphthyl each of which may be optionally substituted by one or more substituents independently selected from lower alkyl, lower alkoxy, halogen, haloloweralkyl, nitro, nitrile aminocarbonyl, loweralkoxycarbonyl, amino, loweralkylamino, or di-loweralkylamino, and heteroaryl is a monocyclic aromatic heterocyclic ring having 5 ring members and having as heteroatoms one or two N atoms or one N atom and one O or S atom, or a monocyclic aromatic heterocyclic ring having 6 ring members and having as heteroatoms one or two N atoms, or a bicyclic aromatic heterocyclic ring system having one such 5 or 6 membered monocyclic aromatic heterocyclic ring fused to a benzene ring, $R^2$ is a monocyclic aromatic heterocyclic ring having 6 ring members and having as heteroatoms one or two N atoms or a bicyclic aromatic heterocyclic ring system having one such 6 membered monocyclic aromatic heterocyclic ring fused to a benzene ring, which may be optionally substituted as for aryl provided that, said bicyclic heterocyclic radical is connected to the amino nitrogen of formula I via such heterocyclic ring;

$R^3$ is hydrogen, lower alkyl, cycloalkyl, cycloalkenyl, cycloalkyl(loweralkyl), aryl, aryl(loweralkyl), a group of formula —$NR^4R^5$, or a group of formula $OR^6$, in which $R^4$ is hydrogen, lower alkyl, aryl or aryl(loweralkyl) and $R^5$ is hydrogen, lower alkyl, —CO(loweralkyl), aryl, —COaryl, aryl(loweralkyl), cycloalkyl or cycloalkyl(loweralkyl), or $R^4$ and $R^5$ together with the nitrogen atom to which they are both attached represent azetidino pyrrolidino, piperidino, hexahydroazepino, morpholino or piperazino which may be optionally substituted by lower alkyl, aryl or aryl(loweralkyl), and $R^6$ is lower alkyl cycloalkyl, cycloalkyl(loweralkyl), aryl or aryl(loweralkyl), wherein aryl is as defined for $R^1$ and cycloalkyl or cycloalkenyl is a mono-, bi-, tri-, or tetracyclic hydrocarbon group of 3 to 12 carbon atoms.

40. A compound of the formula

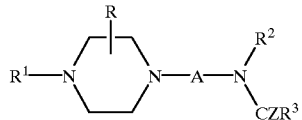

I or a pharmaceutically acceptable acid addition salt thereof, wherein

A is an alkylene chain of 2 to 4 carbon atoms optionally substituted by one or more lower alkyl groups;

Z is oxygen or sulphur;

R is hydrogen or lower alkyl;

$R^1$ is a bicyclic oxygen-containing aryl radical of the formula

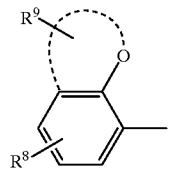

wherein the heterocyclic oxygen-containing ring has 5 to 7 ring members, said heterocyclic ring being non-aromatic and optionally having one further hetero ring member selected from —O—, —S—, —$SO_2$ or $NR^7$, $R^2$ is a monocyclic aromatic heterocyclic ring having 6 ring members and having as heteroatoms one or two N atoms or a bicyclic aromatic heterocyclic ring system having one such 6 membered monocyclic aromatic heterocyclic ring fused to a benzene ring, which may be optionally substituted by one or more substituents independently selected from lower alkyl, lower alkoxy, halogen, haloloweralkyl, nitro, nitrite, aminocarbonyl, loweralkoxycarbonyl, amino, loweralkylamino, or di-loweralkylamino, provided that, said bicyclic heterocyclic radical is connected to the amino nitrogen of formula I via such heterocyclic ring;

$R^3$ is hydrogen, lower alkyl, cycloalkyl, cycloalkenyl, cycloalkyl(loweralkyl), aryl, aryl(loweralkyl), a group of formula —$NR^4R^5$, or a group of formula $OR^6$, in which $R^4$ is hydrogen, lower alkyl, aryl or aryl (loweralkyl)

$R^5$ is hydrogen, lower alkyl, —CO(loweralkyl), aryl, —COaryl, aryl(loweralkyl), cycloalkyl or cycloalkyl (loweralkyl), or $R^4$ and $R^5$ together with the nitrogen atom to which they are both attached represent azetidino, pyrrolidino, piperidino, hexahydroazepino, morpholino or piperazino which may be optionally substituted by lower alkyl, aryl or aryl(loweralkyl), $R^6$ is lower alkyl cycloalkyl, cycloalkyl(loweralkyl), aryl, or aryl(loweralkyl), wherein aryl is as defined for $R^1$ and cycloalkyl or cycloalkenyl is a mono-, bi-, tri-, or tetracyclic hydrocarbon group of 3 to 12 carbon atoms;

$R^7$ is hydrogen or lower alkyl; and $R^8$ and $R^9$ represent hydrogen or one or more substituents independently selected from lower alkyl, halogen, hydroxy, loweralkoxy, hydroxyloweralkyl, loweralkoxyloweralkyl, loweralkanoyloxy (loweralkyl), loweralkylcarbonyl, loweralkylcarbonyl (loweralkyl), amino, loweralkylamino or di-loweralkylamino.

41. A compound of the formula

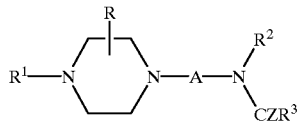

or a pharmaceutically acceptable acid addition salt thereof, wherein

A is an alkylene chain of 2 to 4 carbon atoms optionally substituted by one or more lower alkyl groups;

Z is oxygen or sulphur;

R is hydrogen or lower alkyl;

$R^1$ is a bicyclic oxygen-containing aryl radical of the formula

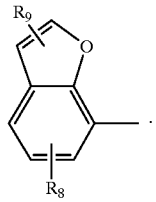

$R^2$ is a monocyclic aromatic heterocyclic ring having 6 ring members and having as heteroatoms one or two N atoms or a bicyclic aromatic heterocyclic ring system having one such 6 membered monocyclic aromatic heterocyclic ring fused to a benzene ring, which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, provided that, said bicyclic heterocyclic radical is connected to the amino nitrogen of formula I via such heterocyclic ring;

$R^3$ is hydrogen, lower alkyl, cycloalkyl, cycloalkenyl, cycloalkyl(loweralkyl), aryl, aryl(loweralkyl), a group of formula —$NR^4R^5$, or a group of formula $OR^6$, in which $R^4$ is hydrogen, lower alkyl, aryl or aryl (loweralkyl) and $R^5$ is hydrogen, lower alkyl, —CO (loweralkyl), aryl, —COaryl, aryl(loweralkyl), cycloalkyl or cycloalkyl(loweralkyl), or $R^4$ and $R^5$ together with the nitrogen atom to which they are both attached represent azetidino, pyrrolidino, piperidino, hexahydroazepino, morpholino or piperazino which may be optionally substituted by lower alkyl, aryl or aryl(loweralkyl);

$R^6$ is lower alkyl, cycloalkyl, cycloalkyl(loweralkyl), aryl, or aryl(loweralkyl), wherein aryl is as defined for $R^1$ and cycloalkyl or cycloalkenyl is a mono-, bi-, tri-, or tetracyclic hydrocarbon group of 3 to 12 carbon atoms; and $R^8$ and $R^9$ represent hydrogen or one or more substituents independently selected from lower alkyl, halogen, hydroxy, loweralkoxy, hydroxyloweralkyl, loweralkoxyloweralkyl, loweralkanoyloxy (loweralkyl), loweralkylcarbonyl, loweralkylcarbonyl (loweralkyl), amino, loweralkylamino or di-loweralkylamino.

42. A compound of the formula

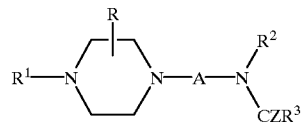

or a pharmaceutically acceptable acid addition salt thereof, wherein

A is an alkylene chain of 2 to 4 carbon atoms optionally substituted by one or more lower alkyl groups, Z is oxygen or sulphur;

R is hydrogen or lower alkyl;

$R^1$ is a bicyclic oxygen-containing aryl radical selected from the group consisting of:

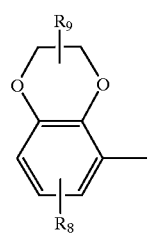

(a)

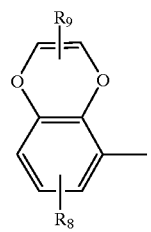

(b)

(c) 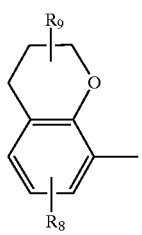

(d) 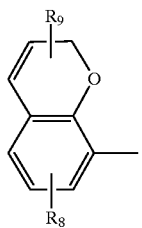

(e) 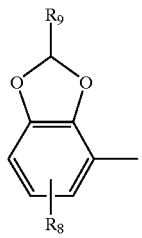

(f) 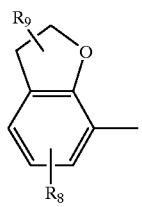

(g) 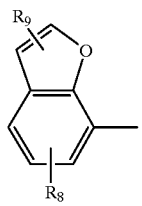

(h) 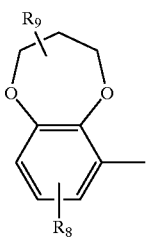

(i) 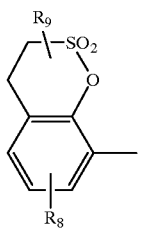

(j) 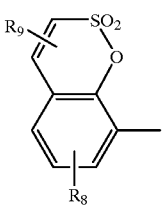

(k) 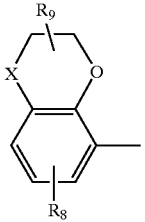

$R^2$ is a monocyclic aromatic heterocyclic ring having 6 ring members and having as heteroatoms one or two N atoms or a bicyclic aromatic heterocyclic ring system having one such 6 membered monocyclic aromatic heterocyclic ring fused to a benzene ring, which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, provided that, said bicyclic heterocyclic radical is connected to the amino nitrogen of formula I via such heterocyclic ring;

$R^3$ is hydrogen, lower alkyl, cycloalkyl, cycloalkenyl, cycloalkyl(loweralkyl), aryl, aryl(loweralkyl), a group of formula —$NR^4R^5$, or a group of formula $OR^6$, in which $R^4$ is hydrogen, lower alkyl, aryl or aryl (loweralkyl)

$R^5$ is hydrogen, lower alkyl, —CO(loweralkyl), aryl, —COaryl, aryl(loweralkyl), cycloalkyl or cycloalkyl (loweralkyl), or $R^4$ and $R^5$ together with the nitrogen atom to which they are both attached represent azetidino, pyrrolidino, piperidino, hexahydroazepino, morpholino or piperazino which may be optionally substituted by lower alkyl, aryl or aryl(loweralkyl), $R^6$ is lower alkyl, cycloalkyl, cycloalkyl(loweralkyl), aryl, or aryl(loweralkyl), wherein aryl is as defined for $R^1$ and cycloalkyl or cycloalkenyl is a mono-, bi-, tri-, or tetracyclic hydrocarbon group of 3 to 12 carbon atoms; and $R^8$ and $R^9$ represent hydrogen or one or more substituents independently selected from lower alkyl, halogen, hydroxy, loweralkoxy, hydroxyloweralkyl, loweralkoxyloweralkyl, loweralkanoyloxy (loweralkyl), loweralkylcarbonyl, loweralkylcarbonyl (loweralkyl), amino, loweralkylamino or di-loweralkylamino.

43. A method for treating anxiety in a mammal which comprises administering to said mammal an effective amount of a compound claimed in claim 1.

* * * * *